United States Patent [19]
Koch et al.

[11] Patent Number: 5,632,740
[45] Date of Patent: May 27, 1997

[54] ILLUMINATED LEADING PROBE DEVICE

[75] Inventors: Frank Koch; Dirk Pawlowski; M. Spitznas, all of Bonn; Wolfgang Neuberger, Monchen-Gladbach, all of Germany

[73] Assignee: Ceram Optec Industries, Inc., East Longmeadow, Mass.

[21] Appl. No.: 302,123

[22] Filed: Sep. 7, 1994

Related U.S. Application Data

[63] Continuation of Ser. No. 750,114, Aug. 26, 1991, abandoned, which is a continuation-in-part of Ser. No. 647,817, Jan. 30, 1991, abandoned.

[51] Int. Cl.$^6$ .................................................. A61B 1/015
[52] U.S. Cl. .................................. 606/4; 606/2; 606/15; 606/107; 606/170; 600/178; 600/182; 362/32; 362/804
[58] Field of Search .................... 606/2, 4, 6, 13–17, 606/107, 170; 604/20–22, 27; 607/88–93; 128/4–7; 362/32, 804; 600/160–178, 182, 199, 200

[56] References Cited

U.S. PATENT DOCUMENTS

| | | | |
|---|---|---|---|
| 3,659,607 | 5/1972 | Banko | 606/170 |
| 3,728,998 | 4/1973 | Heine | 128/9 |
| 4,082,946 | 4/1978 | Heine et al. | 128/6 |
| 4,820,264 | 4/1989 | Matsui et al. | 604/21 |
| 5,143,435 | 9/1992 | Kikuchi | 362/32 |

*Primary Examiner*—David M. Shay
*Attorney, Agent, or Firm*—Bolesh J. Skutnik

[57] ABSTRACT

A method and a device is described. The probe device is a leading probe for surgical procedures which includes both instrument access and illumination. The leading probe device includes an annular arrangement of a plurality of light transmission fibers about a central instrument-receiving working channel. The leading probe may be fixed on the outer wall of the eye by a notched footplate with suitable suture material. Alternatively, the present invention device may have an appropriate adhesive member for securing the leading probe at the surface of the eyeball.

10 Claims, 3 Drawing Sheets

5,632,740

ILLUMINATED LEADING PROBE DEVICE

REFERENCE TO RELATED CASE

This is a continuation of application Ser. No. 07/750,114, filed Aug. 26, 1991 now abandoned, which in turn is a continuation-in-part of application Ser. No. 07/647,817, filed Jan. 30, 1991, now abandoned.

BACKGROUND OF THE INVENTION

1. Field Of The Invention

The present invention is directed to surgical instruments for use in vitrectomies and the like, and more specifically to an improved illuminated leading probe device for intraocular surgery which enables the user to do bimanual operations within the eye. It is also directed to a method of using the devices. The device of the present invention relies upon defined optical fiber and probe configuration, as more fully developed below.

2. Prior Art Statement

Operations in the so-called vitreous body of the eye (vitrectomies) are carried out under the operating microscope. Various lighting techniques and devices have been developed for such surgeries. To obtain reflux-free illumination during such procedures, the illuminating beam and the observation beam have to be separated. This is accomplished by introducing illuminating beams into the eyeball. The entry site for such devices is in all cases the so-called "pars plana" at the transition between the anterior ⅓ and the posterior ⅔ of the eyeball. Up to now, the following illumination systems are known:

1. Metallic sleeves containing illuminated glass fibers in their walls are slid over the vitrectomy instruments and are introduced into the eye together with those instruments. Due to the materials used, the diameter of such sleeves is relatively large and their illuminating capacity relatively low. Moreover, the light emerging from the sleeve illuminates only the tip of the vitrectomy instrument and the tissues immediately adjacent to it. The rest of the vitreous cavity remains dark.

2. Fiber-optic probes consist of a bundle of glass fibers assembled in a metal tube, carried through a hand-piece and connected to a light source. Such probes have a diameter of about 20 gauge. For their insertion into the eye, they require a separate incision in the pars plana. Their advantage lies in the reduction of the total diameter of the instruments to be introduced into the eye. Due to the materials used, the illumination obtained is relatively low. When employing wide angle observation systems, such probes need to be retracted as far as possible, because their angle of illumination is rather small. For this reason, they often slide out of the entry site and need to be re-introduced again. Their main disadvantage is the fact that they completely occupy one hand of the surgeon so that the actual surgical manipulations have to be performed with the one remaining hand.

The so-called "Deckenlampen" (literally "ceiling light") light sources are short, stubby light guides consisting of one single thick fiber or a bundle of several fibers. They are introduced into the eye in the region of the pars plana and are fixed upon the eyeball. As a disadvantage, such "ceiling lights" require their own additional incision in the pars plana, thus increasing the trauma of the surgical intervention. In addition, the materials employed so far do not carry much light and their angle of illumination is not particularly wide.

European Patent Application Publication Number 0201280 A2, filed by Tokyo Kogaku Kikai Kabishiki Kaisha, describes a short tube with a length of only a few millimeters and light fibers integrated into its wall. The tube is introduced into the vitreous body at the pars plana and fixed on the outer wall of the eye by means of a foot plate. The lumen of the tube carries an O-ring and serves to introduce an infusion into the eye. The device is meant to render both hands of the surgeon free for active bi-manual intraocular surgery. The device is not very bright and the illuminating angle is rather small. The tube cannot be used for the introduction of instruments other than the infusion. Due to the rather axial illuminating beam, the surgeon must use one hand to guide the course of the light beam in the eye. Bi-manual maneuvers can only be carried out if an assistant directs the light beam, which is rather difficult to do because of the lack of space in the surgical field outside the eye. For the operation, one then separately uses the appliance with the prior art light source which leads to a highly focused overall lighting and may lead to light toxicity to the back of the eye.

Prior art disadvantages are effectively eliminated and replaced by the present invention. Light conducting fibers with extremely small diameters are used so that the entire diameter of the part of the leading probe device placed into the "Pars plana" entails only about 1.5 mm to 1.7 mm. In the present invention device, simultaneous illumination and instrument insertion is achieved, eliminating a separate opening, reducing risks, increasing light guidance and illumination accuracy and freeing a hand so that bimanual operations are easily accomplished by the surgeon.

SUMMARY OF THE INVENTION

A method and a device is described. The device is a leading probe for surgical procedures which facilitates instrument access and provides wide angle illumination. The leading probe device includes an annular arrangement of a plurality of light transmission fibers about a central instrument-receiving working channel. The leading probe may be fixed to the wall of the eye by a notched footplate with suitable suture material. Alternatively, the present invention device may have an appropriate adhesive member for securing the leading probe at the surface of the eyeball.

BRIEF DESCRIPTION OF THE DRAWINGS

The present invention will be more fully understood when the specification herein is taken in conjunction with the appended drawings, in which.

DETAILED DESCRIPTION OF INVENTION

Figure 1:
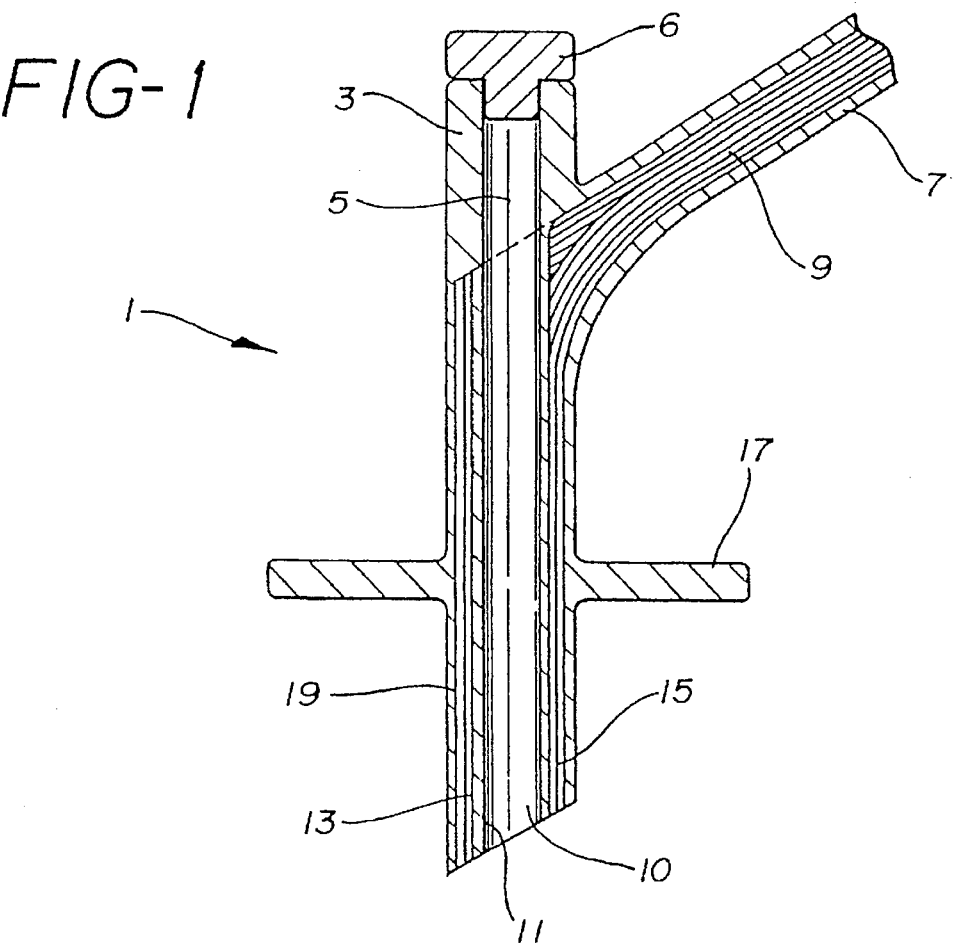
FIG. 1. shows a side cut view of the operating end of a leading probe device of the present invention.

The present invention leading probe device introduces an illuminating system which reaches only a few millimeters into the vitreous cavity, is fixed on the outer wall of the eye and does not require an additional entry site. It can be introduced through one or more of the pars plana incisions needed anyway for the surgical intervention (2 for surgical instruments, 1 for infusion). Each device of the illuminating system consists of a thin tube with an outer diameter of about 1.5 mm, carrying in its wall about 20 light conducting fibers which form an illuminating annular-like ring around the lumen of the tube. The free lumen or working channel of the tube remains for the introduction of surgical instruments into the eye. The small outer diameter is accomplished by the specific material of the light fibers employed, which carry more light than the fibers used in prior art systems.

The present invention leading probe device provides a free working channel to place instruments into the eye during an operation. Furthermore, the surgeon is capable of working with two hands since the lighting is carried along with the instruments. The light conducting fibers consist of material of high numerical aperture for insertion, resulting in a wider cornering angle (about 70°) for the fibers. This in turn means that a large number of light conducting fibers are assignable to every leading probe device (e.g. 20 fibers each) In addition, there is a very small chance of injury to the back of the eye. This invention has the very important advantage of minimizing strong direct lighting which, over a relatively long period of time during an operation, can lead to irreversible damage to the eye.

The fibers employed in the present invention consist of a tissue compatible plastic and have a diameter of no bigger than 0.25 mm. In addition, the fibers are characterized by a high numeric aperture, e.g. a numeric aperture of 0.4 to 0.7. For example, one such device containing fibers of high numeric aperture may produce an angle of illumination of 70 degrees at the tip of the fibers. The leading probe device may be fixed on the outer wall of the eye with suitable suture material by means of a notched foot plate. Alternatively, the present invention device may have an appropriate adhesive mechanism for securing the leading probe at the surface of the eye. At the distal end of the tube, the light fibers are carried to one side, leaving between them a funnel-shaped entrance into the working channel of the tube. The emerging light fibers are then bundled and connected to an external light source. The working channel of the tube is accessible through an opening with a specific diameter in the middle of the leading probe device. The working channel can be used to introduce a variety of interchangeable surgical instruments into the vitreous cavity. It can also receive an infusion line which is secured in place by a bayonet-like fitting. Special plugs made of plastic or metal may serve to temporarily occlude the working channel during phases of surgery while one of the tubes is not in use. The working channel may also be reduced in diameter by insertion of a reducer made of plastic or metal.

During a vitrectomy one or more of these leading probe devices are used. The main goal of this invention is to provide an independent lighting source so that the operator may utilize both hands when operating. Thus, two present invention devices may be used simultaneously by a single surgeon, one in each of two incisions. One or both devices may be used for instrument insertion and one for infusion purposes. As mentioned earlier, any illuminated leading probe device not in use during the operation can be sealed with a plug to prevent the loss of eye fluid. In one preferred embodiment, the inner diameter of the leading probe device calls for approximately 0.01 mm clearance. Using a surgical instrument of almost exactly the same diameter inserted therethrough likewise reduces the loss of fluid from the lens perimeter.

This invention, then, concomitantly allows the operator to place instruments into the eye with automatic lighting so that the inner eye cut and the working environment are entirely illuminated by any combination of opened or closed tubes. Moreover, an even greater advantage is provided by the relatively large distance between the fibers and the instruments used for the operation, thereby resulting in minimal shaded area. In addition, with the present invention, it is possible to regulate the strength of the light by means of a filter at the external light source. Furthermore, since the illuminating system of the present invention reaches only a few millimeters into the vitreous cavity, the emerging light remains at a distance from the back of the eye that minimizes the danger of over-illuminating that area. The fibers consist of synthetic plastic and are therefore elastic, reducing risk of fractures and increasing useful life. For additional protection the fibers are preferably coated with a plastic covering. Since the invention gives double access and therefore double utilization, additional protective coating is used for the leading probe.

A further advantage of this invention is the elimination of the possibility for dirt particles to appear on the fibers which are inserted in the eye, since the fibers are maintained within or about the probe during an entire surgery.

The invention has the following advantages:

a.) Capability for having two free hands for active bi-manual surgical manipulation in the vitreous body during all phases of the intervention.

b.) Excellent intensity of illumination.

c.) Optimal illumination of the entire vitreous cavity owing to the wide numeric aperture of the fibers.

d.) Avoidance of retinal damage owing to diffuse illumination of the entire vitreous cavity. This invention allows light to be conducted from an external source to the leading probe in the eye wall e.) No traumatization by additional entry sites.

f.) Automatic following-movements of the illumination with all movements of the surgical instruments.

g.) Minimized surgical trauma owing to the small outer diameter of the device.

h.) Free exchange between surgical instruments and infusion. This enables the surgeon to choose the openings with the most favorable angle with regard to the ocular structures to be operated on.

Referring now to FIG. 1 there is shown a side cut view of the operating end of a leading probe device 1. It has a main straight wall 3 with working channel 5 for insertion of surgical instruments, including infusion. Plug 6 closes the upper end of working channel 5 when leading probe device 1 is not being used during an operation. This prevents fluid loss from the eye. Side wall with protective cover 7 contains a bundle of fibers connected to a light source. The fibers 9 run through and wrap around the inside of device 1 so that they terminate within an annular port formed by lower outer wall 19 and inner wall 11. Individual optical fibers 13 and 15 are shown which terminate at the leading probe end 10, as shown. Notched footplate 17 is used to attach to the wall of the eyeball with suitable suture material and leading probe end 10 penetrates and is inserted into the eyeball.

Figure 2:
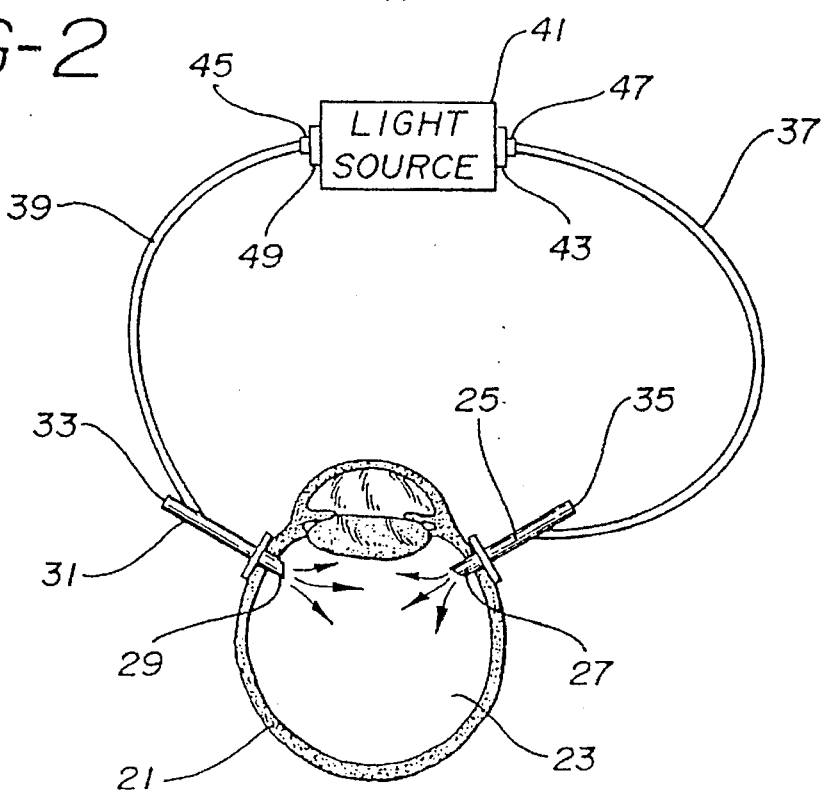
FIG. 2. is a side cut view of an eyeball utilizing dual leading probes of the present invention.

As shown in FIG. 2, two such devices similar to that of device of FIG. 1 are shown inserted into eyeball 23 by penetrating eyeball wall 21. Thus devices 25 and 31 have their leading probe ends 27 and 29 inserted into eyeball 23, as shown. A side tube with protective cover 37 and 39 for each of devices 25 and 31 is connected to a light source 41 for illumination of the cluster of optical fibers (not shown). Light source 41 has filters 43 and 49 attached thereto. Attached to filters 43 and 49 are adapters 47 and 45 for the optical fiber bundles (not shown) carried in side tubes with protective covers 37 and 39. The user may insert instruments into working channels 33 and 35 for direct insertion thereof into eyeball 23 and bimanual operations may be performed with simultaneous use of the surgical instrument and the illumination of the leading probe devices 25 and 31

Figure 3:
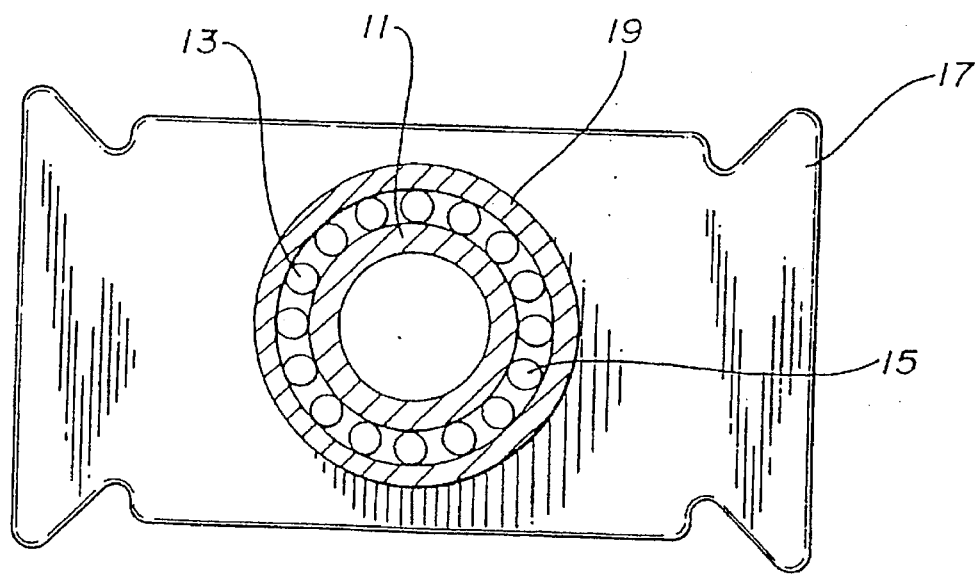
FIG. 3. is a bottom cut view of a present invention device showing a notched footplate attachment means.

FIG. 3 shows a bottom cut view of the device shown in FIG. 1 and like parts are like numbered. Here, the annular arrangement of the optical fibers typified by fibers 13 and 15, is shown. It is the arrangement of optical fibers around the working channel which creates the substantial advantages of the present invention.

Figure 4:
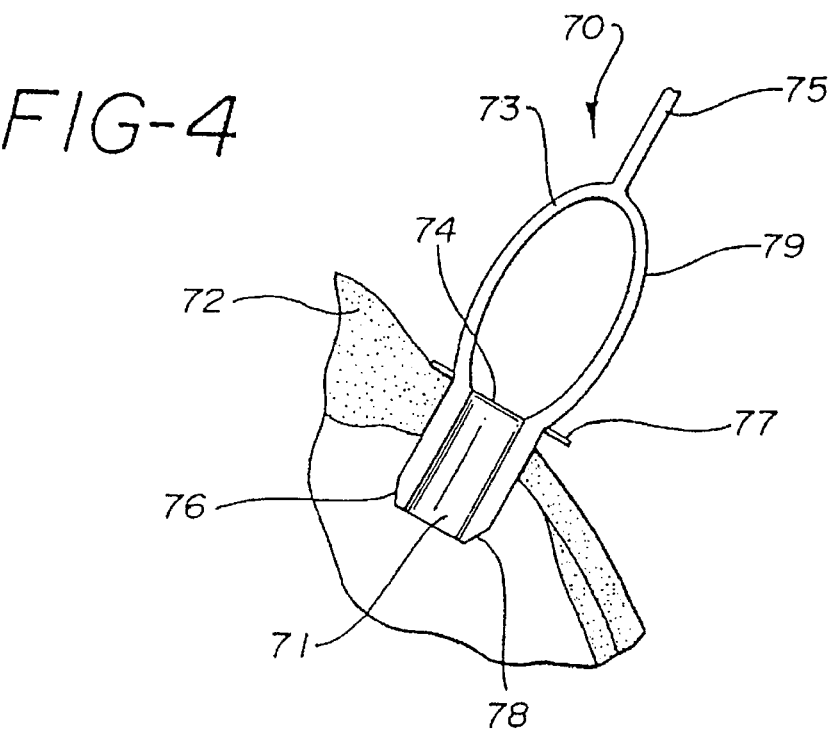
FIG. 4. shows a side cut view of a present invention device inserted into an eyeball with an alternative means of connecting optic fiber bundles to the leading probe.

FIG. 4 shows alternative present invention device 70 wherein a single leading probe device is inserted into the eye through eyeball surface 72 and attached via attachment means 77. Leading probe end 71 has a reduced diameter for easier insertion as shown by angled edges 76, 78. Side tube with protective cover 75 is attached to a light source (not shown). One arrangement may be as follows: a cluster of optical fibers (not shown) carried within side tube with protective cover 75 is separated into two smaller optical fiber clusters (not shown) carried within light guides 73 and 79. The user may insert an instrument into working channel 74 and through eyeball wall 72.

Figure 5:
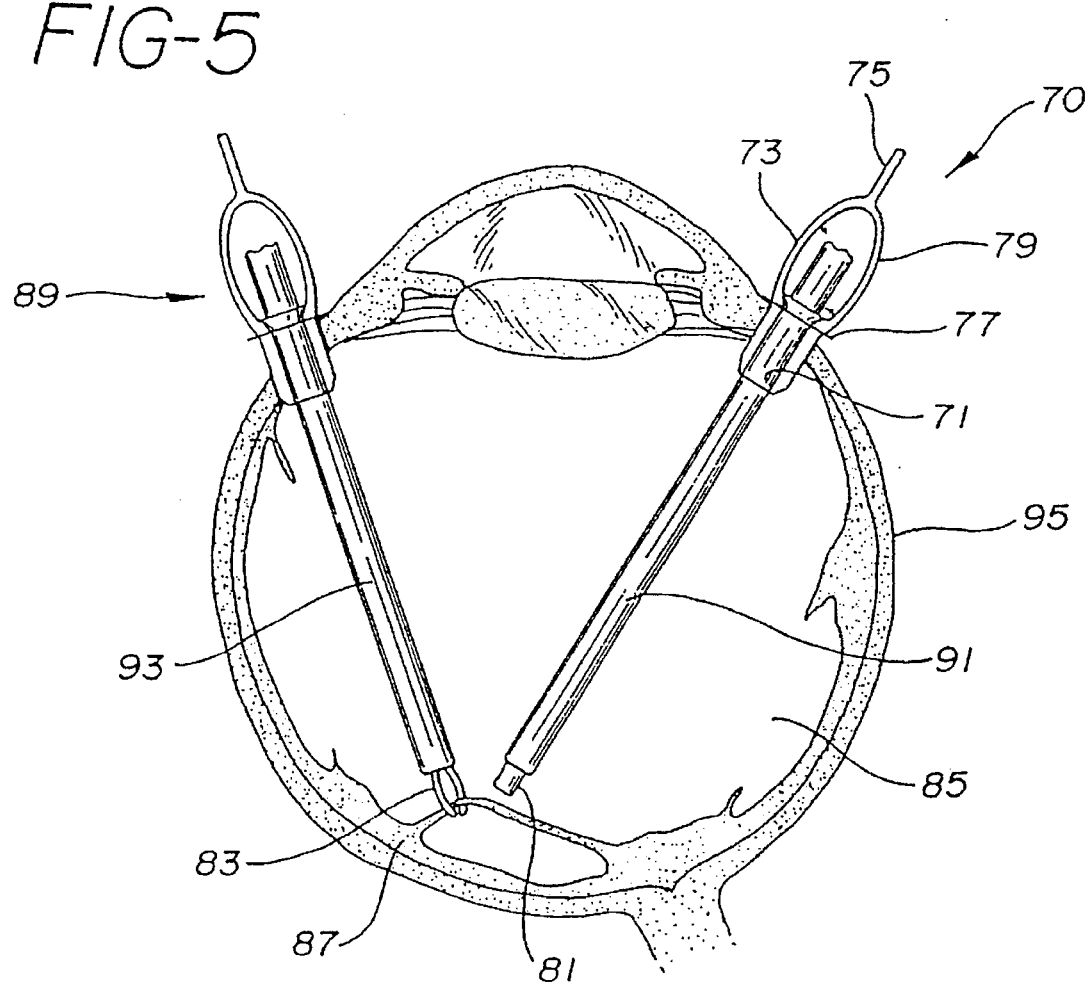
FIG. 5. shows an example of two active surgical instruments being inserted through two leading probe devices during an operation.

FIG. 5 shows an example of two active instruments being inserted into the eye through two illuminated leading probe devices during an operation. Device 70 is similar to the device of FIG. 4 and like parts are like numbered. Surgical cutting instrument 81 in instrument guide 91 is inserted through leading probe end 71. Device 70 containing cutting instrument 81 is used in conjunction with similar device 89 containing surgical forceps 83 in instrument guide 93. Both devices are inserted through eyeball wall 95 into eyeball 85 and the surgical instruments are shown performing a procedure on tissue 87 at the back of eyeball 85.

Obviously, numerous modifications and variations of the present invention are possible in light of the above teachings. It is therefore understood that within the scope of the appended claims, the invention may be practiced otherwise than as specifically described herein.

What is claimed is:

1. A probe device for use in medical procedures in an eye, comprising:

a generally cylindrical main wall;

a foot plate about an intermediate portion of said main wall;

said foot plate including means for abutting an outer surface of said eye;

a generally cylindrical working channel coaxial with said main wall;

said working channel including a probe leading end;

said probe leading end including means for enabling entry of said probe leading end through an eyeball wall into said eye;

said working channel permitting the passage of at least one of a surgical instrument or an optical device therethrough from outside said eye though said probe leading end to an interior of said eye;

means for permitting plugging of an outer end of said working channel, whereby leakage of a fluid from an interior of said eye is prevented;

a side tube joining said main wall at an angle to an axis thereof;

a bundle of optical fibers passing through said side tube into an interior of said main wall outside said working channel;

said bundle of optical fibers passing through said side tube from outside said side tube into said main wall;

said bundle of optical fibers terminating in a pattern at said probe leading end; and said pattern being an annulus surrounding said working channel.

2. A probe device according to claim 1, wherein said means for enabling entry includes a bevelled end on said probe leading end.

3. A probe device according to claim 1, wherein said means for enabling entry includes an angled edge about a periphery of said probe leading end.

4. A probe device according to claim 1, further comprising means for connecting a light source to an outer end of said bundle of optical fibers.

5. A probe device according to claim 1, wherein a numeric aperture of said optical fibers is from about 0.4 to about 0.7.

6. A probe device according to claim 1, wherein said optical fibers produce an angle of illumination of about 70 degrees at a tip thereof.

7. A probe device according to claim 1, wherein said foot plate further includes means for enabling affixation thereof to said eyeball wall.

8. A probe device according to claim 7, wherein said means for enabling affixation includes at least one notch in said foot plate.

9. A probe device according to claim 1, wherein said optical fibers have diameters no bigger than 0.25 mm.

10. A probe device according to claim 9, wherein said optical fibers have diameters from about 0.1 to about 0.25 mm.

\* \* \* \* \*